(12) United States Patent
Michaeli et al.

(10) Patent No.: US 10,821,287 B2
(45) Date of Patent: Nov. 3, 2020

(54) BIOELECTRICAL MODULATION USING ROTATING OR SPATIALLY-SELECTIVE ELECTROMAGNETIC FIELDS

(71) Applicant: REGENTS OF THE UNIVERSITY OF MINNESOTA, Minneapolis, MN (US)

(72) Inventors: Shalom Michaeli, Minneapolis, MN (US); Silvia Mangia, Minneapolis, MN (US); Olli Grohn, Kuopio (FI); Artem Shatillo, Kuopio (FI); Lauri Lehto, Minneapolis, MN (US); Matthew Johnson, Minneapolis, MN (US); Simeng Zhang, Minneapolis, MN (US); Julia Slopsema, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 635 days.

(21) Appl. No.: 15/485,544

(22) Filed: Apr. 12, 2017

(65) Prior Publication Data
US 2017/0296825 A1    Oct. 19, 2017

Related U.S. Application Data

(60) Provisional application No. 62/322,046, filed on Apr. 13, 2016.

(51) Int. Cl.
*A61N 1/36* (2006.01)
*A61N 1/05* (2006.01)

(52) U.S. Cl.
CPC ....... *A61N 1/36182* (2013.01); *A61N 1/0534* (2013.01); *A61N 1/36192* (2013.01)

(58) Field of Classification Search
CPC .............. A61N 1/36182; A61N 1/0534; A61N 1/36192
See application file for complete search history.

(56) References Cited

U.S. PATENT DOCUMENTS

| | | | |
|---|---|---|---|
| 7,181,288 B1 * | 2/2007 | Rezai ................... | A61N 1/0529 607/116 |
| 2009/0118806 A1 * | 5/2009 | Vetter ................ | A61B 5/04001 607/116 |

(Continued)

OTHER PUBLICATIONS

Butson CR, McIntyre CC. Role of electrode design on the volume of tissue activated during deep brain stimulation. Journal of neural engineering 2006;3:1-8.

(Continued)

*Primary Examiner* — Catherine M Voorhees
*Assistant Examiner* — Roland Dinga
(74) *Attorney, Agent, or Firm* — Quarles & Brady LLP (57) ABSTRACT

Described here are bioelectric modulation systems and methods for generating rotating or spatially-selective electromagnetic fields. A modulation system includes a multi-channel electrode with independently controllable electrode channels that can be operated to generate rotating electromagnetic fields that stimulate cells regardless of their orientation, or to generate spatially-selective electromagnetic fields that preferentially stimulate cells oriented along a particular direction. The bioelectric modulation system may be implemented for stimulation of neurons or other electrically active cells. The bioelectric modulation described here may be used for a variety applications including deep brain stimulation (DBS), spinal cord and vagus nerve stimulation, stimulation of myocardial (heart) tissue, and directional stimulation of muscles.

20 Claims, 5 Drawing Sheets

(56) References Cited

U.S. PATENT DOCUMENTS

| | | | | |
|---|---|---|---|---|
| 2011/0313236 A1* | 12/2011 | Valente | .................... | A61N 2/02 600/15 |
| 2013/0085361 A1* | 4/2013 | Mercanzini | ........ | A61B 5/04001 600/377 |

OTHER PUBLICATIONS

Butson CR, McIntyre CC. Current steering to control the volume of tissue activated during deep brain stimulation. Brain stimulation 2008;1:7-15.

Chaturvedi A, Foutz TJ, McIntyre CC. Current steering to activate targeted neural pathways during deep brain stimulation of the subthalamic region. Brain stimulation 2012;5:369-77.

Connolly AT, Vetter RJ, Hetke JF, Teplitzky BA, Kipke DR, Pellinen DS, et al. A Novel Lead Design for Modulation and Sensing of Deep Brain Structures. IEEE transactions on bio-medical engineering 2016;63:148-57.

Johnson MD, Franklin RK, Gibson MD, Brown RB, Kipke DR. Implantable microelectrode arrays for simultaneous electrophysiological and neurochemical recordings. Journal of neuroscience methods 2008;174:62-70.

Keane M, Deyo S, Abosch A, Bajwa JA, Johnson MD. Improved spatial targeting with directionally segmented deep brain stimulation leads for treating essential tremor. Journal of neural engineering 2012;9:046005.

LaRoy, J.J.L. et al. "Multitine Deep Brain Stimulation Leads to Shape Neural Activation in Three Dimensions" Journal of Medical Devices, 2014; 8(2): 020919.

Martens HC, Toader E, Decre MM, Anderson DJ, Vetter R, Kipke DR, et al. Spatial steering of deep brain stimulation volumes using a novel lead design. Clinical neurophysiology : official journal of the International Federation of Clinical Neurophysiology 2011;122:558-66.

Pollo C, Kaelin-Lang A, Oertel MF, Stieglitz L, Taub E, Fuhr P, et al. Directional deep brain stimulation: an intraoperative double-blind pilot study. Brain : a journal of neurology 2014;137:2015-26.

Van Dijk KJ, Verhagen R, Chaturvedi A, McIntyre CC, Bour LJ, Heida C, et al. A novel lead design enables selective deep brain stimulation of neural populations in the subthalamic region. Journal of neural engineering 2015;12:046003.

\* cited by examiner

FIG. 9 ized applications are also hereby incorporated by reference.

BIOELECTRICAL MODULATION USING ROTATING OR SPATIALLY-SELECTIVE ELECTROMAGNETIC FIELDS

CROSS-REFERENCE TO RELATED APPLICATIONS

This application is based on, claims priority to, and incorporates herein by reference in its entirety U.S. Provisional Application Ser. No. 62/322,046, filed Apr. 13, 2016, and entitled, "Deep Brain Stimulation System That Generates Rotating Or Spatially-Selective Electromagnetic Fields." The references cited in the above provisional patent application are also hereby incorporated by reference.

This invention was made with government support under NS103569 awarded by the National Institutes of Health. The government has certain rights in the invention.

BACKGROUND

Electrical signals and gradients in the body are involved in such activities as cellular communication and activation/suppression of cellular functions. In electrically excitable cells such as neurons and muscle cells, for example, changes in electric fields in one cell can quickly affect adjacent or more distant cells. The orientation of excitable cells in relation to electric fields and relative to nearby cells and tissue can impact their behavior. Specific changes in electrical fields experienced by cells can thus have significant effects in the body.

For example, stimulation of cells in the brain can have powerful neurological and psychiatric effects. One way of bringing about such effects in the brain is via deep brain stimulation ("DBS"), which involves using electrodes to send electrical impulses to specific targets in the brain. DBS has been found to be an effective treatment option for such disorders as mild to severe Parkinson's disease (PD). Because DBS is still a relatively new technique in clinical practice and the mechanisms of action of DBS are not fully understood, the technique requires significant improvement and optimization. In particular, there is a need to develop energy efficient DBS strategies and DBS systems that allow for selective stimulation of specific neuronal populations such that safe and effective neuromodulation can be implemented.

Recent studies have indicated that electrical modulation of axons can play an important role in deep brain stimulation's therapeutic mechanisms. It would be advantageous to have a DBS system that allows for local and selective stimulation of particular structures in the brain (e.g., subthalamic nucleus) without perturbing surrounding areas (e.g., motor capsule). Precision of the stimulation can dictate if the desired treatment response is achieved and if the desired neuronal pathway has been selectively and effectively stimulated. Precision can also dictate the severity of side effects caused by the stimulation.

Traditional DBS uses electric fields that are not directionally controlled. Recent progress in target selection has led to the utilization of multichannel electrodes to provide current steering and shaping of the area of the stimulation. However, while these approaches have aimed to optimize the amplitude of the electrical field over a specified volume of interest, they do not utilize the direction of the electrical fields to specifically stimulate axons based on the orientation of those axons.

The ability to selectively stimulate distinct axonal bundles with different orientations provides a novel biomedical and neuroscience research tool, along with a new dimension for optimization of treatment response, as axonal modulation has been recognized to play a critical role in therapeutic mechanisms. Therefore, development of novel bioelectrical modulation strategies that include more energy-efficient and orientation-selective pulse paradigms would be useful in, for example, modulating specific neuronal populations to more effectively achieve desired outcomes.

SUMMARY OF THE DISCLOSURE

Systems and methods described in the present disclosure provide for bioelectrical modulation using a multichannel electrode with at least two independently controllable electrode channels. Phase-modulated control signals may be sent to at least two independently controllable electrode channels to operate the multichannel electrode to generate an electromagnetic field. The phase-modulated control signals may provide a different phase to each of the at least two independently controllable electrode channels such that the electromagnetic field generated by the multichannel electrode rotates in a space.

The foregoing and other aspects and advantages will appear from the following description. In the description, reference is made to the accompanying drawings which form a part hereof, and in which there is shown by way of illustration one or more preferred embodiments. Such embodiments do not necessarily represent the full scope of the invention, however, and reference is made therefore to the claims and herein for interpreting the scope of the invention.

DETAILED DESCRIPTION

Figure 1:
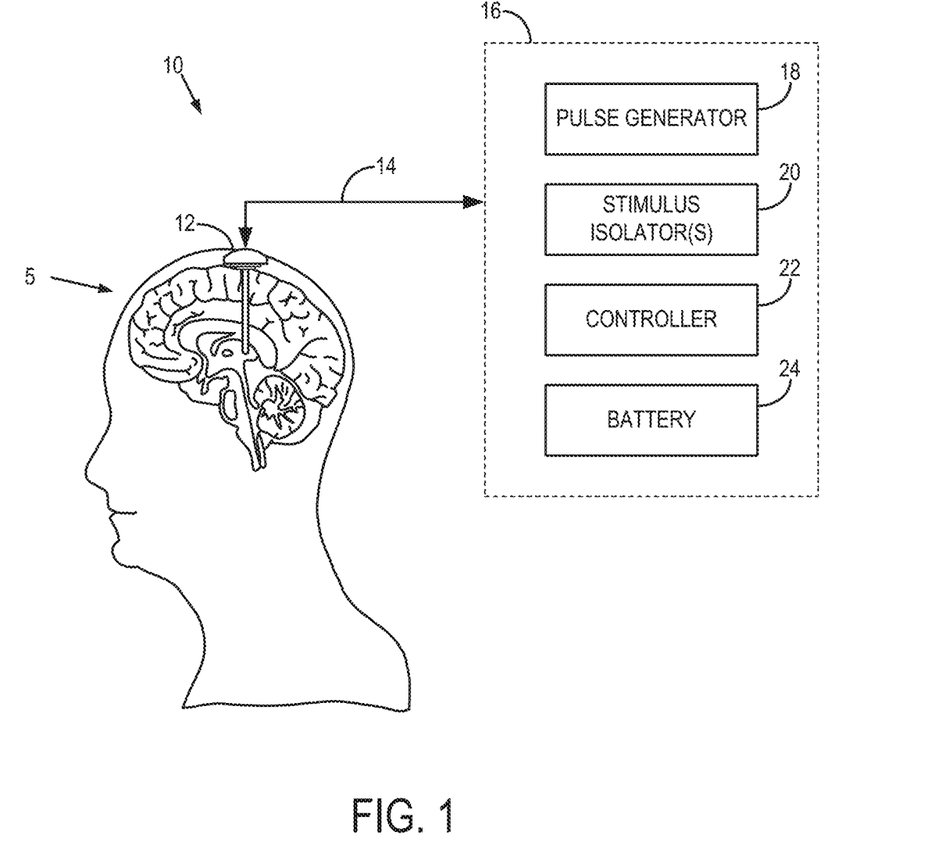
FIG. 1 is an example bioelectric modulation system having a multichannel electrode with independently controllable electrode channels that can generate rotating or spatially selective magnetic fields. The illustrated implementation is deep brain stimulation (DBS).

Described here are bioelectric modulation systems and methods for generating rotating electromagnetic fields or spatially-selective electromagnetic fields in tissue, which may be, for example, portions of the brain or spinal cord, one or more nerves (such as the vagus nerve), etc. One such bioelectric modulation system, as applied to the nervous system of a subject 5, is shown in FIG. 1. The system 10 includes one or more multichannel electrodes 12 that can be operated to generate rotating electromagnetic fields that stimulate cells (here, axons) regardless of their orientation, or to generate spatially selective electromagnetic fields that preferentially stimulate cells having a particular orientation.

In some example implementations, the system 10 may be configured to effectuate deep brain stimulation (DBS). The multichannel electrode 12 may be implanted in the brain of a subject, and electrically connected via an insulated cable 14 to a neurostimulator 16, which may be implanted in the subject's torso (e.g., below the subject's clavicle). In some configurations, the multichannel electrode 12 can wirelessly communicate with the neurostimulator 16. The neurostimulator 16 includes a pulse generator 18, one or more stimulus isolators 20, a controller 22, and a battery pack 24 that powers the DBS system 10.

Figure 2A:
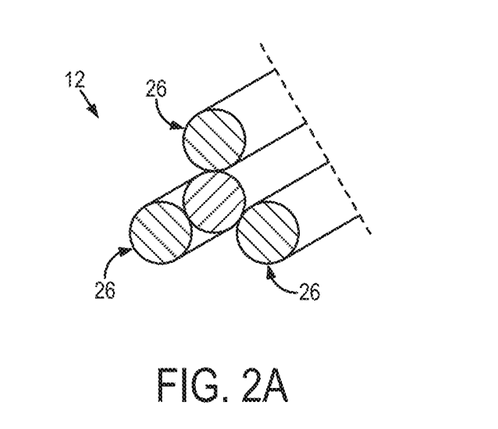
FIG. 2A is an isometric view of an example multichannel electrode.
Figure 2B:
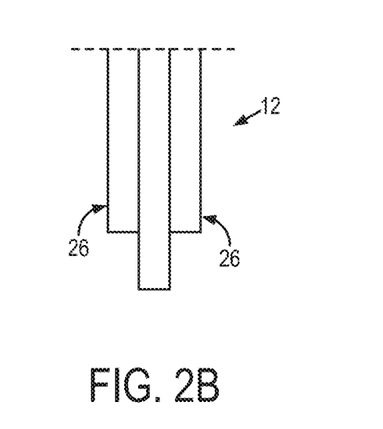
FIG. 2B is a top view of an example multichannel electrode.

One example multichannel electrode 12 is shown in FIGS. 2A and 2B. The multichannel electrode 12 includes several independently controllable and uncoupled electrode channels 26. The multichannel electrode 12 can be composed of a material such as a platinum-iridium alloy or tungsten, or other biologically inert conducting materials deemed suitable.

To control the electromagnetic field orientation in a two-dimensional ("2D") plane located at the tip of the multichannel electrode 12, three or more independently controllable electrode channels can be used. Thus, in some configurations, the multichannel electrode 12 can be a tripolar electrode to generate orientational and rotating field stimulation in a plane. To control the electromagnetic field orientation in three dimensions, four or more independently controllable electrode channels can be used. The position of the inner channel 26 in FIGS. 2A and 2B as well as the relative distances between each channel 26 can be varied. As one example, the inner channel 26 can be close to one of the other three channels 26 shown in FIGS. 2A and 2B. In this example, varying the position of the inner electrode channel 26 relative to the outer electrode channels 26 provides flexibility to generate asymmetry in the electromagnetic fields.

Figure 2C:
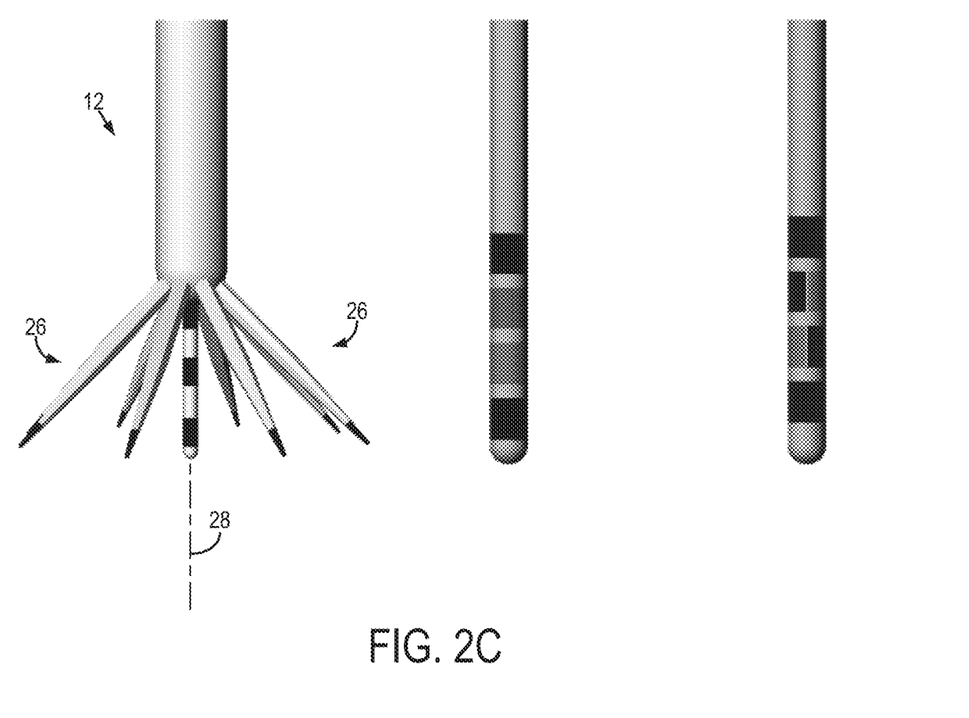
FIG. 2C is an example of a multichannel electrode having multiple tines that are angled away from a longitudinal axis of the multichannel electrode (left), and the Medtronic 3389 (middle) and St. Jude Medical 6172 (right) leads which could be used for generating orientation selective and rotating field stimulations using two or more channels.

Another example multichannel electrode 12 is shown in FIG. 2C. This multichannel electrode 12 includes multiple independently controllable electrode channels 26 that can be angled away from a longitudinal axis 28 of the multichannel electrode 12. An example of such a multi-tined electrode is described by JJL LaRoy, et al., in "Multi-tine deep brain stimulation leads to shape neural activation in three dimensions," *Journal of Medical Devices*, 2014; 8(2): 020919.

As mentioned above, the system 10 can include one multichannel electrode 12, but can also include more than one multichannel electrode 12. In this latter configuration, the multiple multichannel electrodes 12 can provide more flexibility to shape the electromagnetic field for selective excitation of particular neuronal populations.

The independently controllable electrode channel design of the multichannel electrode 12 allows for current, or voltage, to be delivered in each channel 26 with different amplitude modulation, frequency modulation, phase modulation, or combinations thereof. Thus, the system 10 allows for the independent control of the amplitude, frequency, and phase of the current, or voltage, in each channel 26. For example, the amplitude, frequency, or phase in a given channel may be constant or modulated according to a channel-specific function. Using this independent control of the individual electrode channels 26 in the multichannel electrode 12, the system 10 can generate rotating electromagnetic fields that are capable of stimulating neurons or other cells regardless of their orientation, or can generate spatially-selective electromagnetic fields to preferentially stimulate neurons oriented along specific directions.

The neurostimulator 16 sends signals to each channel 26 in the multichannel electrode 12 to generate electromagnetic fields to stimulate neurons. Each channel 26 of the multichannel electrode 26 can be independently driven under the control of stimulation signals generated by the pulse generator 18 and provided to separate stimulus isolators 20 under control of the controller 22, which may include a digital-to-analog converter.

Figure 3:
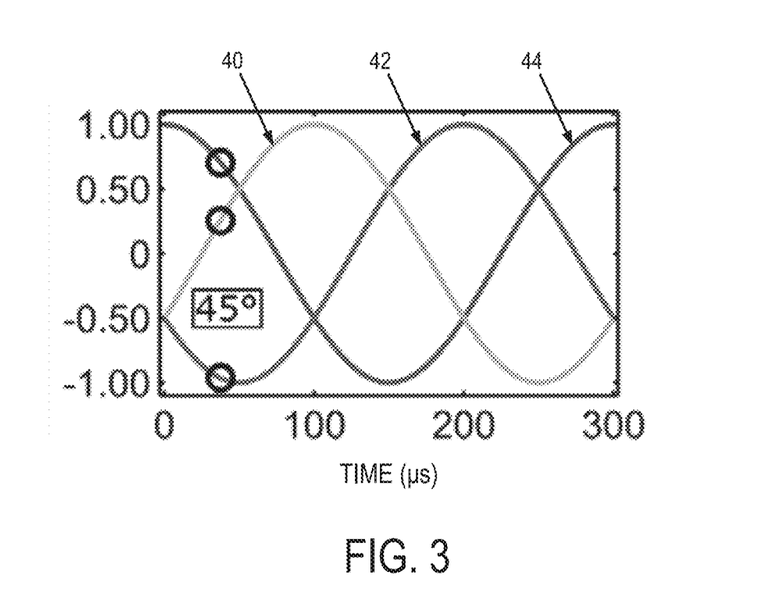
FIG. 3 is an example of amplitude and phase modulated control signals provided to three independently controllable electrode channels to generate a rotating electromagnetic field.

The controller 22 may be used to send channel-specific control signals to the electrode channels 26. In one non-limiting example, the control signals provided to the channels 26 in the multichannel electrode 12 can be cosine amplitude modulation functions according to the following equation:

$$I_i = I_{0i} \cos\left(\frac{2\pi t}{T} + \phi_i\right); \quad (1)$$

where $I_{0i}$ is the maximal amplitude of electromagnetic field for the $i^{th}$ channel and $\phi_i$ is the phase delivered to the $i^{th}$ channel. The phase difference between the electrode channels is chosen between 0-2π, and can be set as a constant for each channel. To allow the electromagnetic field to rotate around a circle, the phase difference between electrode channels can be selected as ⅔π for a three channel electrode. It is noted that the phase differences between the contacts do not necessarily need to be equal and could vary in time. The phase differences between the channels are then varied and combined with the modulating amplitude of the electromagnetic field in each channel. An example of such control signals are shown in FIG. 3, in which lines 40, 42, and 44 correspond with channels 1, 2, and 3, respectively. It is noted that in other implementations, the control signals may correspond with sinusoidal or non-sinusoidal functions other than cosine. That is, the control signals provided to the channels 26 can be, for example, square, rectangular, triangular, spiked, trapezoidal, sawtooth, Gaussian, exponential or other functions as deemed suitable for different applications.

With the appropriate independent control of the electrode channels, a two-dimensional pattern of stimulation (e.g., a circle or ellipsoid) can be formed in various implementations. Notably, the electromagnetic fields can be generated to have a directionally dependent intensity, which can be spatially dependent or time dependent. Namely, gradients of the electric fields, dE/dl and dE/dt, could be generated. The directionally dependent intensity can allow for preferential stimulation of neurons oriented along particular directions, such as fiber bundles with anisotropic geometry, or a group of axons oriented predominantly in one direction.

Figure 4:
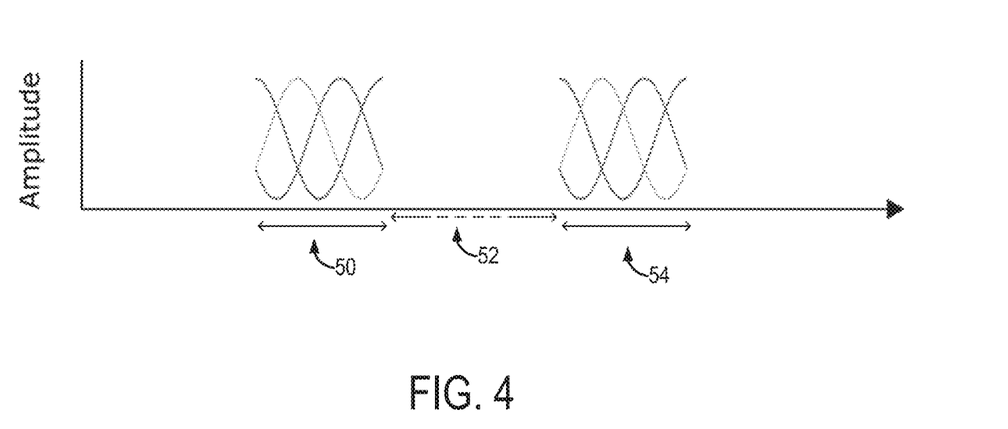
FIG. 4 is an example of a pulsed stimulation scheme in which control signals are provided to a multichannel electrode in a block paradigm.

In some examples of operation, the control signals can be provided to the multichannel electrode 12 in a pulsed scheme. An example of such a pulsed scheme is shown in FIG. 4. In this example pulsed scheme, the control signals may be provided in a block paradigm of, for example, 60 second "off" periods (52) interspersed with 18 second on periods (50, 54), during which the control signals are provided to the multichannel electrode 12. It will be appreciated that other block paradigms can be designed and implemented based on the desired application.

To determine some example parameters that can be used to drive the multichannel electrode 12 to generate angularly selective electromagnetic fields, simulations were performed. In one specific example, two cases were modeled: crossing white matter bundles and crossing individual axons in grey matter. These geometries are representative of axon orientations encountered in the brain. The COMSOL software packages were used for the simulations of the rotating and spatially selective fields. To solve the potential field due to the oscillating currents, COMSOL was used to solve the Poisson equation of the system.

Figure 5:
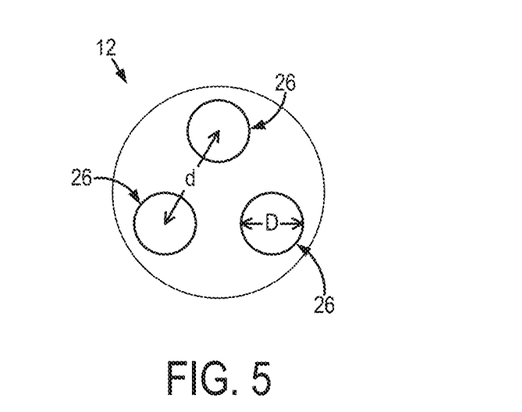
FIG. 5 is an example geometry of a multichannel electrode.

In this example modeled system, which is illustrated in FIG. 5, the diameter, D, of each electrode channel 26 was varied between 50-150 μm, and the distance between channels 26 was not greater than three times the diameter of the individual channels 26 (i.e., d<3D). This choice of dimensions was selected so each channel would not be separated from each other at the distance greater than 3D because beyond that distance of separation the influence of the channels on each other may be significantly reduced such that each channel behaves like a monopolar electrode.

The simulated multichannel electrode was composed of three 200 μm diameter cylinders embedded into brain tissue. The conductivity of brain tissue was selected as 0.3 Siemens/meter. The simulated multichannel electrode generated rotating electric fields based on differences in phases of the amplitude modulated currents, as given by the following equations:

$$I_1 = I_0 \cos\left(\frac{2\pi t}{T}\right); \quad (2)$$

$$I_2 = I_{01} \cos\left(\frac{2\pi t}{T} + \phi_1\right); \quad (3)$$

$$I_3 = I_{02} \cos\left(\frac{2\pi t}{T} + \phi_2\right); \quad (4)$$

where $I_i$ are the currents delivered to the $i^{th}$ channel, and $\phi_i$ are the phase differences between different channels and were chosen in this example to be $$\phi_1 = \frac{2}{3}\pi \text{ and } \phi_2 = -\frac{2}{3}\pi.$$

The maximum amplitude, $I_0$, can be selected as a value such as 1 or 2 mA.

Figure 6:
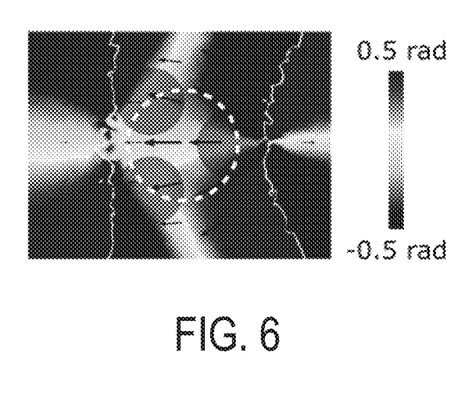
FIG. 6 is a simulation of an example electric field generated using the control signals shown in FIG. 3 and electrode of FIG. 5

The localized orientation of the electric field on x-y plane induced by the three-channel design is shown in FIG. 6. In FIG. 6, the orientation of the x-y components of the electric field vectors (indicated by arrows) are further illustrated at zero degrees for the nominal electric field orientation on a plane 50 μm under the electrode.

Figure 7:
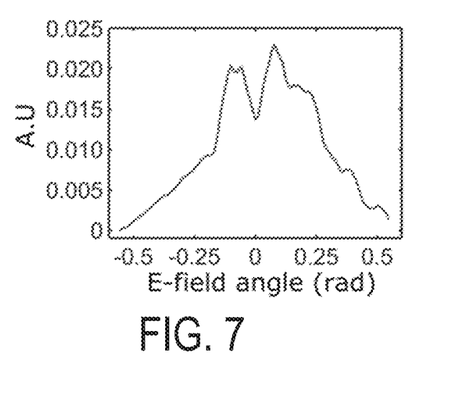
FIG. 7 is a distribution of electromagnetic field orientations in the white dashed circle shown in FIG. 6.

FIG. 7 shows the distribution of the electric field orientations inside the area indicated by the white dashed circle in FIG. 6. This distribution shows that creating spatial selectivity of a unidirectional field can be implemented with a three channel electrode. It is noted that analytically defined waveforms and geometrical configuration of the channels can be selected to improve the spatial selectivity of the electromagnetic fields in different implementations.

Figure 8:
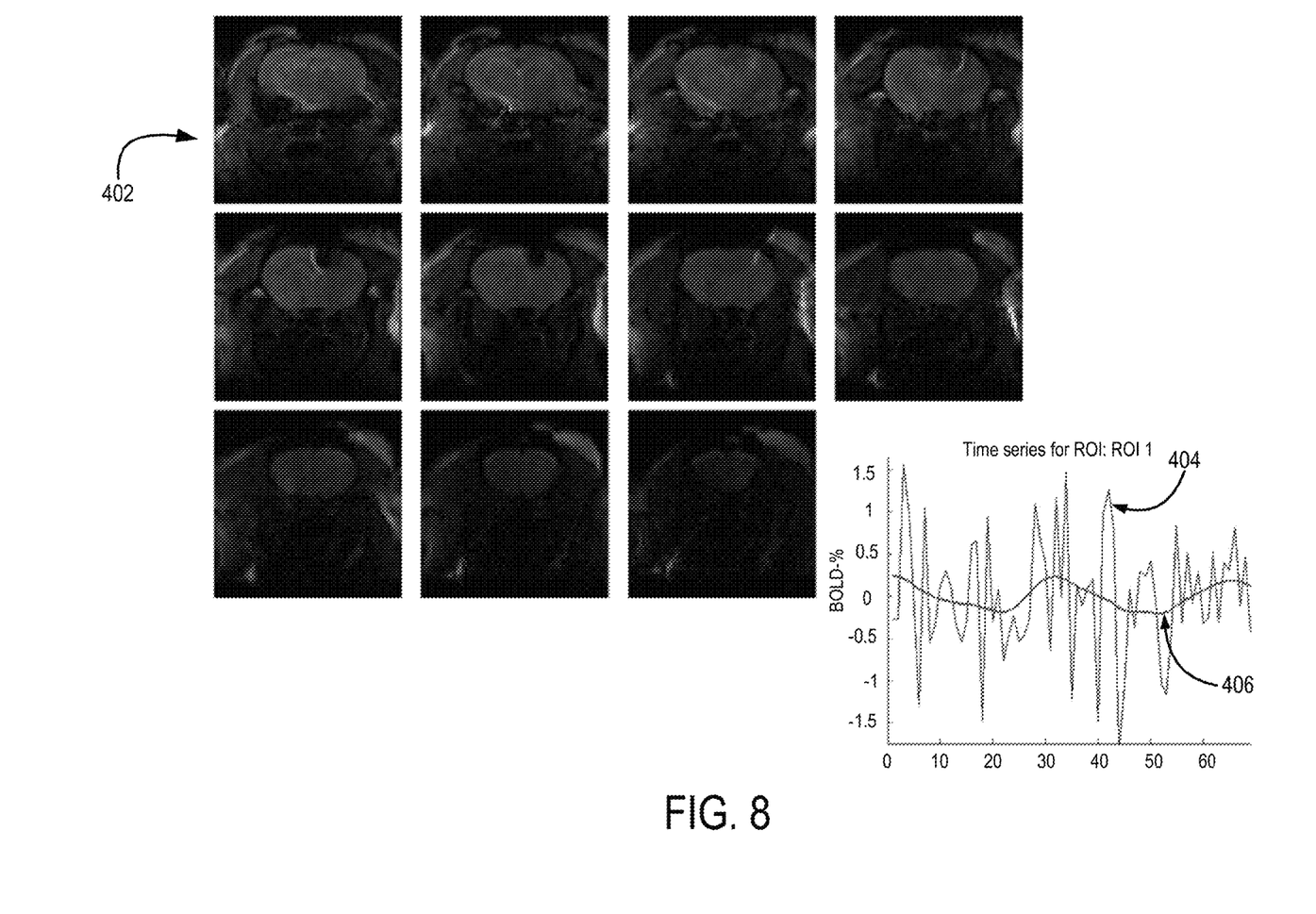
FIG. 8 is a series of functional magnetic resonance images and a corresponding fMRI signal time course compared to the control signals provided to a multichannel electrode to generate an electromagnetic field primarily oriented perpendicular to an axonal orientation in rat corpus callosum.
Figure 9:
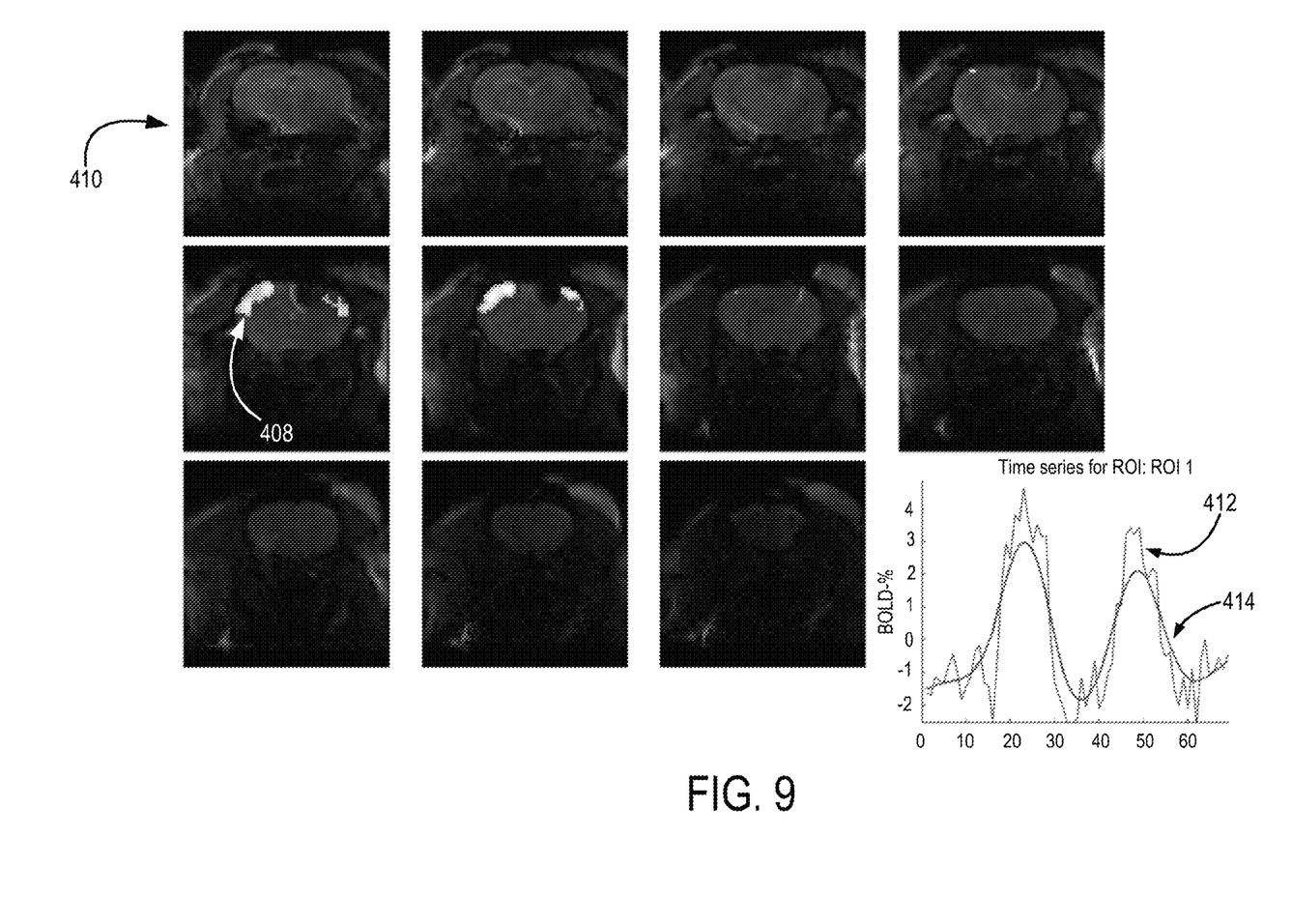
FIG. 9 is a series of functional magnetic resonance images and a corresponding functional magnetic resonance imaging (fMRI) signal time course compared to the control signals provided to a multichannel electrode to generate an electromagnetic field primarily oriented parallel to an axonal orientation in rat corpus callosum, thereby stimulating axons in the corpus callosum.

FIGS. 8 and 9 show an example implementation of the DBS system described here. In this example, a three-channel electrode was implanted in the right side of a rat's corpus callosum, where the orientation of the fibers is well defined. In FIG. 8, the electromagnetic field is generated to be primarily oriented at an angle of 90 degrees relative to the fiber orientation in the corpus callosum. A functional magnetic resonance image (fMRI) 402 taken at this point in the experiment showed no neuronal activation. A time series of the fMRI signals (line labeled 404) for a region-of-interest ("ROI") in the somatosensory cortex (which is connected to the corpus callosum), provided in the graphic located at the bottom-right of FIG. 8, showed no relation to the time series of the DBS control signals (line labeled 406).

In FIG. 9, the orientation of the control signals delivered to the electrode channels were adjusted so the electromagnetic field was oriented parallel to the fiber orientation. As a result, neuronal activation 408 was induced in the somatosensory cortex ROI, as seen in the fMRI images 410. As provided in the graphic at the bottom-right of FIG. 9, the time series of the fMRI signals (line labeled 412) similarly closely followed that of the DBS control signals (line labeled 414).

The multichannel electrode designs, together with independent control of channel-specific amplitude, frequency, and phase modulated waveforms, may thus be used to generate rotating and spatially-selective electromagnetic fields for use in bioelectric modulation. The systems described here can be used, for example, to increase the efficiency and robustness of the electrical stimulation of excitable cells. In implementations involving neurons, for example, efficiency can be improved using a rotating electromagnetic field when stimulating isotropically distributed axonal ensembles. The systems described here can also be used to achieve spatially specific stimulation using asymmetrical rotations, with directionally dependent intensity generated using different amplitude and phase modulation of the electromagnetic field that allows the excitation threshold to be lower in a predetermined direction.

As noted above, the bioelectric stimulation system may be applied to stimulate electrically active cells other than neurons or nerves. For example, this could be applied to stimulation of myocardial (heart) tissue and direction stimulation of muscles. Astrocytes, for example, can have ramified filopodia that could also be modulated by the rotating field approach. The neuromodulation system described here could be used for spinal cord stimulation (SCS) and vagus nerve stimulation.

The present disclosure has described one or more preferred embodiments, and it should be appreciated that many equivalents, alternatives, variations, and modifications, aside from those expressly stated, are possible and within the scope of the invention.

The invention claimed is:

1. A system for bioelectric modulation, comprising:
   a multichannel electrode having at least three independently controllable electrode channels arranged in a non-linear array; and
   a controller configured to send phase-modulated control signals to the at least three independently controllable electrode channels to operate the multichannel electrode to generate an electromagnetic field,
   the phase-modulated control signals providing a different time-invariant or time-dependent phase function to each of the at least three independently controllable electrode channels so that the electromagnetic field generated by the multichannel electrode is fixed in time or undergoes time-dependent re-orientation, respectively,
   the time-dependent phase function producing one or more frequency bands of stimulation.

2. The system of claim 1, wherein each of the phase-modulated control signals has an amplitude that is modulated by the controller so that the electromagnetic field generated by the multichannel electrode has a time-invariant or time-dependent directionally dependent intensity.

3. The system of claim 2, wherein the time-dependent and directionally dependent intensity is:
   asymmetrical in the plane, and
   defined by differently modulating the amplitudes of the phase-modulated control signals provided to the independently controllable electrode channels.

4. The system of claim 3, wherein the controller differently modulates the amplitudes of the phase-modulated control signals so that the directionally dependent intensity of the electromagnetic field is greater than a threshold value only along a predetermined direction in the plane.

5. The system of claim 3, wherein the controller differently modulates the amplitudes of the phase-modulated control signals so that the directionally dependent intensity of the electromagnetic field is greater than a threshold value along at least two predetermined directions in the plane.

6. The system of claim 3, wherein differently modulating the amplitudes of the phase-modulated control signals provided to the independently controllable electrode channels further comprises assigning the amplitudes of the phase-modulated control signals provided to the independently controllable electrode channels to an amplitude-modulated pulse or a square pulse at each of the independently controlled channels.

7. The system of claim 2, wherein the directionally dependent intensity is symmetrical in the plane and defined by modulating the amplitudes of the phase-modulated control signals provided to the independently controllable electrode channels to be substantially similar.

8. The system of claim 1, wherein the multichannel electrode comprises electrodes made of a biocompatible conducting material.

9. The system of claim 1, wherein the controller comprises a pulse generator and at least three stimulus isolators, and wherein each of the at least three stimulus isolators is electrically coupled to one of the at least three electrode channels so that control signals generated by the pulse generator are independently provided to one of the electrode channels.

10. The system of claim 1, wherein the phase-modulated control signals provide the different time-dependent phase functions to each of the at least three independently controllable electrode channels so that the electromagnetic field spatial gradient undergoes complex trajectories in at least two dimensions and generates temporal electromagnetic field gradients.

11. The system of claim 1, wherein the multichannel electrode extends along a longitudinal axis from a distal end to a proximal end, and includes at least three tines extending outward from the proximal end at an angle with respect to the longitudinal axis.

12. The system of claim 1, wherein the at least three independently controllable electrode channels comprises at least four independently controllable electrode channels,
   wherein three of the at least four independently controllable electrode channels define a plane,
   wherein a fourth independently controllable electrode channel of the at least four independently controllable electrode channels is arranged outside the plane,
   wherein the fourth independently controllable electrode channel is different from the three independently controllable electrode channels arranged in the first plane, and
   wherein the phase-modulated control signals provide a different phase to each of the at least four independently controllable electrode channels so that the electromagnetic field generated by the multichannel electrode undergoes complex re-orientation in three dimensions.

13. A method for bioelectric modulation, comprising sending phase-modulated control signals to at least three independently controllable electrode channels of a multichannel electrode to generate an electromagnetic field, wherein the at least three independently controllable electrode channels are arranged in a non-linear array, and wherein the phase-modulated control signals provide a different time-invariant or time-dependent phase function to each of the at least three independently controllable electrode channels so that the electromagnetic field generated by the multichannel electrode is fixed in time or undergoes time-dependent re-orientation, respectively, the time-dependent phase function producing one or more frequency bands of stimulation.

14. The method of claim 13, further comprising modulating an amplitude of each of the phase-modulated control signals so that the electromagnetic field generated by the multichannel electrode has a time-dependent and directionally dependent intensity.

15. The method of claim 14, wherein the time-dependent and directionally dependent intensity is asymmetrical in the plane and defined by differently modulating the amplitudes of the phase-modulated control signals provided to the independently controllable electrode channels.

16. The method of claim 15, wherein the controller differently modulates the amplitudes of the phase-modulated control signals so that the directionally dependent intensity of the electromagnetic field is greater than a threshold value along at least two predetermined directions in the plane.

17. The method of claim 15, wherein differently modulating the amplitudes of the phase-modulated control signals provided to the independently controllable electrode channels further comprises assigning the amplitudes of the phase-modulated control signals provided to the independently controllable electrode channels to an amplitude-modulated pulse or a square pulse at each of the independently controlled channels.

18. The method of claim 15, further comprising differently modulating the amplitudes of the phase-modulated control signals so that the directionally dependent intensity of the electromagnetic field is greater than a threshold value only along a predetermined direction in the plane.

19. The method of claim 13, wherein control signals are generated by a pulse generator, and wherein at least three stimulus isolators are electrically coupled to one of the at least three electrode channels so that control signals generated by the pulse generator are independently provided to one of the electrode channels.

20. The method of claim 13, wherein phase-modulated control signals are sent to at least four independently controllable electrode channels, and wherein the phase-modulated control signals provide a different time-dependent phase to each of the at least four independently controllable electrode channels so that the electromagnetic field generated by the multichannel electrode undergoes complex re-orientation in three dimensions.

* * * * *